(12) United States Patent
Camarillo et al.

(10) Patent No.: US 10,603,124 B2
(45) Date of Patent: Mar. 31, 2020

(54) METHOD FOR NAVIGATING A ROBOTIC SURGICAL CATHETER

(71) Applicant: The Board of Trustees of the Leland Stanford Junior University, Palo Alto, CA (US)

(72) Inventors: David B. Camarillo, San Francisco, CA (US); Jake A. Sganga, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 297 days.

(21) Appl. No.: 15/806,561

(22) Filed: Nov. 8, 2017

(65) Prior Publication Data
US 2018/0125591 A1 May 10, 2018

Related U.S. Application Data

(60) Provisional application No. 62/419,243, filed on Nov. 8, 2016.

(51) Int. Cl.
*A61B 34/00* (2016.01)
*A61B 34/20* (2016.01)
(Continued)

(52) U.S. Cl.
CPC .............. *A61B 34/32* (2016.02); *A61B 34/20* (2016.02); *A61B 34/30* (2016.02); *A61B 34/71* (2016.02);
(Continued)

(58) Field of Classification Search
CPC ......... A61B 34/20; A61B 34/30; A61B 34/32; A61B 34/71; A61B 2034/2051;
(Continued)

(56) References Cited

U.S. PATENT DOCUMENTS 9,186,046 B2 * 11/2015 Ramamurthy ........... A61B 5/06
2009/0324161 A1 * 12/2009 Prisco ..................... G01L 1/246
385/13
(Continued)

OTHER PUBLICATIONS

Tully et al., "A Filtering Approach for Image-Guided Surgery with a Highly Articulated Surgical Snake Robot," IEEE Transactions on Biomedical Engineering, vol. 9294, No. c, pp. 1-1, 2015.
(Continued)

*Primary Examiner* — Robert T Nguyen
(74) *Attorney, Agent, or Firm* — Lumen Patent Firm

(57) ABSTRACT

Autonomous closed loop control of a flexible tendon-driven continuum manipulator having a sensor at a distal tip is performed by measuring spatial attributes of a sensor at the distal tip and estimating an orientation of a base of an articulating region of the flexible tendon-driven continuum manipulator from a kinematic model and the spatial attributes of the sensor. The manipulator control in a task space uses the estimated orientation, a desired trajectory in the task space, and the position of the sensor at the distal tip. The sensor at the distal tip may be a magnetic sensor, impedance sensor, or optical sensor.

5 Claims, 10 Drawing Sheets

(51) Int. Cl.
   *A61B 34/30*  (2016.01)
   *A61B 34/32*  (2016.01)
   *B25J 9/10*  (2006.01)

(52) U.S. Cl.
   CPC ..... *B25J 9/1075* (2013.01); *A61B 2034/2051* (2016.02); *A61B 2034/2057* (2016.02); *A61B 2034/2061* (2016.02); *A61B 2034/301* (2016.02); *A61B 2034/715* (2016.02); *G05B 2219/45118* (2013.01); *Y10S 901/09* (2013.01)

(58) Field of Classification Search
   CPC .... A61B 2034/2057; A61B 2034/2061; A61B 2034/301; A61B 2034/715; B25J 9/1075; G05B 2219/45118; Y10S 901/09
   See application file for complete search history.

(56) References Cited

U.S. PATENT DOCUMENTS

2011/0319714 A1\* 12/2011 Roelle ................ A61B 1/00006
                                                  600/118
2019/0307517 A1\* 10/2019 Arai ....................... A61B 34/71

OTHER PUBLICATIONS

Bajo et al., "Finding Lost Wrenches: Using Continuum Robots for Contact Detection and Estimation of Contact Location." 2010 IEEE International Conference on Robotics and Automation, Anchorage Convention District.

Walker, "Continuous Backbone "Continuum" Robot Manipulators, ISRN Robotics," ISRN Robotics, vol. 2013 (2013), Article ID 726506.

\* cited by examiner

Fig. 12

1200
Measuring spatial attributes of the sensor at the distal tip of the flexible tendon-driven continuum manipulator, wherein the spatial attributes include a position of the sensor at the distal tip

1202
Estimating an orientation of a base of the articulating region of the flexible tendon-driven continuum manipulator, wherein the orientation is estimated from a kinematic model of the flexible tendon-driven continuum manipulator and from the measured spatial attributes of the sensor at the distal tip of the flexible tendon-driven continuum manipulator

1204
Controlling the flexible tendon-driven continuum manipulator in a task space using the estimated orientation of the base of the articulating region, a desired trajectory in the task space, and the position of the sensor at the distal tip

METHOD FOR NAVIGATING A ROBOTIC SURGICAL CATHETER

CROSS-REFERENCE TO RELATED APPLICATIONS

This application claims priority from U.S. Provisional Patent Application 62/419,243 filed Nov. 8, 2016, which is incorporated herein by reference.

FIELD OF THE INVENTION

The present invention relates generally to methods for controlling continuum manipulators used in minimally invasive surgeries. More specifically, it relates to techniques for autonomous control of flexible tendon-driven continuum manipulators.

BACKGROUND OF THE INVENTION

Tendon-driven continuum manipulators are widely used in minimally invasive surgeries. For example, bronchoscopies are a preferred approach to early diagnosis of lung cancer. In a conventional bronchoscopy procedure, a physician manually steers a long, flexible endoscope through the patient's airways. These steerable endoscopes are a class of tendon-driven continuum manipulators with a proximal handle that articulates the distal tip. Physicians rely on sensor feedback from an on-board camera and, in many procedures, an electromagnetic position sensor at the distal tip of the device. The position sensor is registered to a preoperative computed tomography (CT) of the patient's chest to provide a road map to the target site. Despite low complication rates (2.2%), there is significant variability in the diagnostic yield among institutions.

Robotic control of endoscopes in bronchoscopy procedures can potentially alleviate this variability and potentially improve patient outcomes, but autonomous control has proven difficult given the uncertainty in modeling the robot's interaction with the anatomy. Endoscopes and similar tendon-driven continuum manipulators control the end effector position through pull wires that bend the distal section of the device, referred to as the articulating region. Proximal to the articulating region, a decoupled, passive region complies to obstacles, allowing for atraumatic navigation through sensitive areas. The device's compliance results in unknown conformations as the anatomy applies unsensed constraints during a procedure. This presents significant challenges for traditional task-space control techniques that depend on an accurate model of the manipulator to solve for joint displacements and torques because the unsensed conformations change the response of the device in unintuitive ways.

Techniques that adapt to the environment are necessary for providing more intuitive or autonomous control of these devices in clinical settings. One approach is to introduce additional sensors along the body of the manipulator. Fiber Bragg gratings, for example, provide a potential solution to sensing the curvature of the entire manipulator; however, this technology is not yet clinically available. Another approach analyzes real-time ultrasound images in addition to a distal position sensor to determine the orientation of the device. Yet another approach is based on introducing a second position sensor at the junction of the articulating and passive regions, called the base of the manipulator, the model of the articulating region can be rotated, enabling inverse kinematics for closed-loop control.

Alternatively, the state of the robot may be estimated from the existing sensor at the distal tip of manipulators with a fixed base orientation and no passive section. One such approach, for example, estimates the orientation of the links in the HARP continuum manipulator, which has a "follow the leader" design so that each segment's position and orientation can be calculated relative to the fixed base. This type of estimation does not handle contact with the environment, and does not apply to manipulators with decoupled passive and articulating sections, which is characteristic of the majority of clinical catheters and endoscopes.

Despite these attempts, closed loop control remains a challenge for continuum manipulators having a passive region decoupled from an articulating region, and where the sensor is at the tip and not co-located with the base.

BRIEF SUMMARY OF THE INVENTION

The present invention provides methods to autonomously navigate an endoscope through the constrained anatomy of the lung using only the existing distal tip position sensor. The method controls a tendon-driven manipulator that has decoupled passive and articulating regions similar to existing endoscopes. The method focuses on estimation of the robot's orientation to balance adaptability and a priori knowledge of the robot. Two variations of the method are provided that estimate the rotation of articulating region's base. A first variant uses the measured orientation of the distal position sensor. A second variant uses the measured displacement of the distal position sensor.

In one aspect, the invention provides a method for autonomous closed loop control of a flexible tendon-driven continuum manipulator having a sensor at a distal tip and a passive region decoupled from an articulating region. The method includes measuring spatial attributes of the sensor at the distal tip of the flexible tendon-driven continuum manipulator, wherein the spatial attributes include a position of the sensor at the distal tip; estimating an orientation of a base of an articulating region of the flexible tendon-driven continuum manipulator, wherein the orientation is estimated from a kinematic model of the flexible tendon-driven continuum manipulator and from the measured spatial attributes of the sensor at the distal tip of the flexible tendon-driven continuum manipulator; and controlling the flexible tendon-driven continuum manipulator in a task space using the estimated orientation of the base of the articulating region, a desired trajectory in the task space, and the position of the sensor at the distal tip.

In one implementation of the method, the measured spatial attributes further include an orientation of the sensor at the distal tip of the flexible tendon-driven continuum manipulator; and wherein the orientation is estimated by transforming the orientation and the position to coordinates of the base through a curvature calculated from the kinematic model.

In another implementation of the method, the measured spatial attributes further include a displacement of the sensor at the distal tip of the flexible tendon-driven continuum manipulator; and wherein the orientation is estimated using a non-linear filter, such as an extended or unscented Kalman filter or a particle filter.

The sensor at the distal tip may be a magnetic sensor, impedance sensor, or optical sensor. The sensor at the distal tip may be the only sensor on the articulating region of the flexible tendon-driven continuum manipulator, i.e., there is no need for additional sensors in this method.

BRIEF DESCRIPTION OF THE SEVERAL VIEWS OF THE DRAWINGS

FIG. 12 is a flowchart outlining steps of a method for autonomous closed loop control of a flexible tendon-driven continuum manipulator, according to an embodiment of the invention.

DETAILED DESCRIPTION OF THE INVENTION

Figure 1:
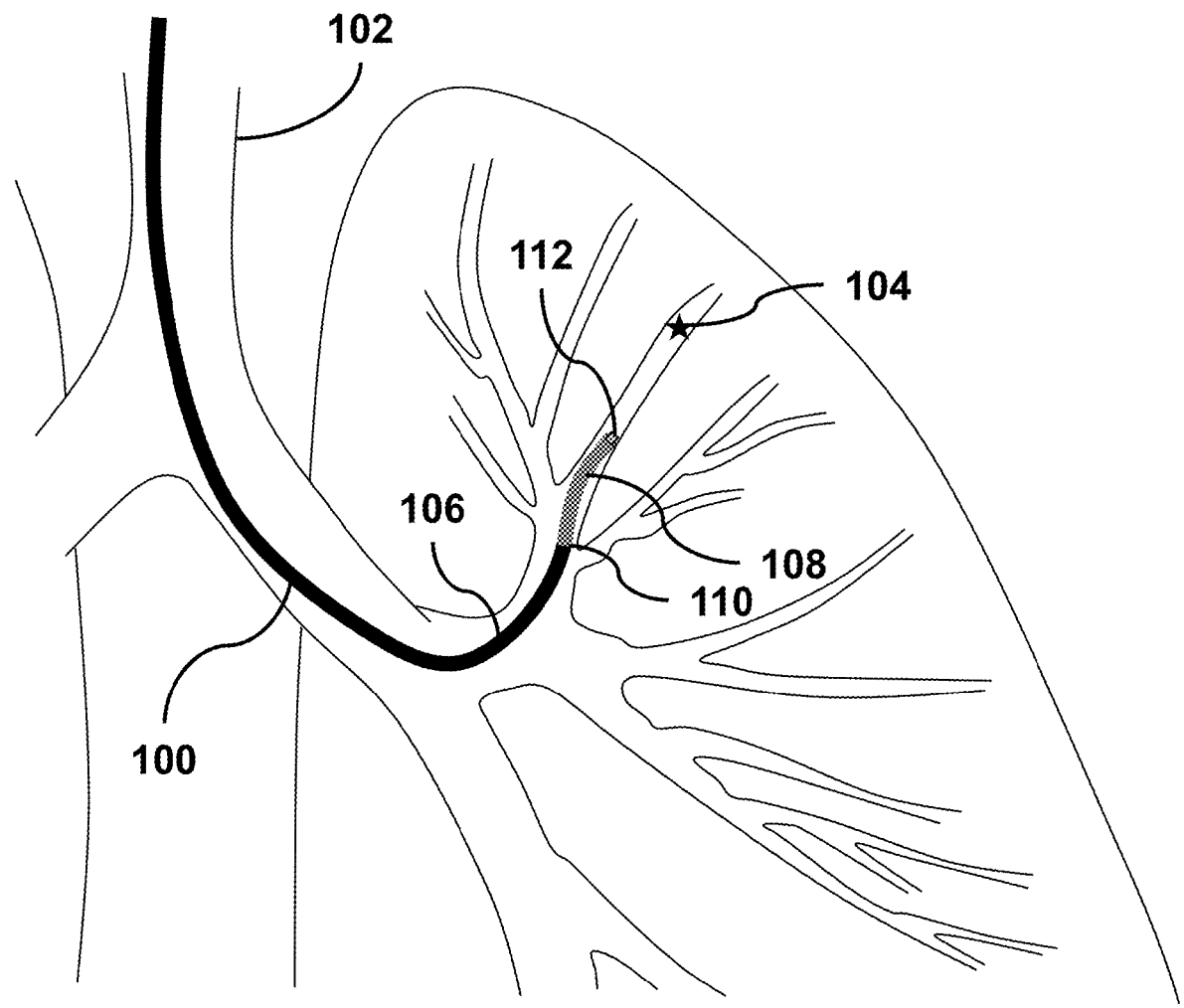
FIG. 1 is a schematic diagram showing an endoscope conforming to the anatomy of the lung's airway during a bronchoscopy procedure.

FIG. 1 shows an embodiment of an autonomous four-tendon continuum manipulator 100 conforming to the anatomy of the lung's airway 102 during a diagnostic procedure in which the manipulator navigates to a goal 104 in the task space. The manipulator 100 has a decoupled passive region 106 and an articulating region 108 whose shape is controlled to guide the manipulator as it is inserted. The articulating region 108 has a base 110 where it joins the passive region and a distal tip 112 where a positioning sensor is located. The sensor at the distal tip is typically a magnetic position sensor, but could also be an impedance sensor or optical sensor. Optical sensing includes standard camera, x-ray, ultrasound, and MRI modalities.

Embodiments of the present invention as based on the insight that the anatomy's effect on the robotic manipulator can be approximated as a rotation of the model-based Jacobian. Two implementations are described that estimate the orientation using a magnetic position sensor at the robot's distal tip, enabling task-space control in unknown, constrained environments. One method, $\hat{R}^\alpha$, determines the orientation of the robot's model using the measured orientation of the distal tip 112. In the second approach, $\hat{R}^{\Delta x}$, a nonlinear filter transforms the tip's measured change in position into an orientation estimate.

In experiments by the inventors, these methods are validated on the manipulator in free space at three pre-rotated positions (α=0°, −45°, −90°) and compared to model-based control and model-less control in an autonomous trajectory-following task through an anatomically accurate silicone phantom of a human lung. The results show that by rotating the model-based Jacobian through either of the two methods presented, feedback control successfully navigates the continuum manipulator farther into the lung phantom than static model-based control and model-less control.

The following notation will be used in the description that follows. Model-based curvature parameters are denoted by $[s_m, \theta_m, \phi_m]$. Motor displacements are denoted $[q_1, \ldots, q_5]$. Task space coordinates are denoted $[x, y, z]$. Model-based Jacobian is denoted by $J_m$. Estimated Jacobian is denoted $\hat{J}$. Constrained Jacobian inverse is denoted $\hat{J}_{cstr}^{-1}$. A vector v expressed in frame D is denoted $^D v$. Rotation from frame C to frame D is denoted $_C^D R$. Z-Y-Z Euler angles are denoted $[\alpha, \beta, \gamma]$. Estimated Euler angles between the base and ground frames are denoted $[\hat{\alpha}, \hat{\beta}, \hat{\gamma}]$. Rotation about the Z, Y, Z axes by angles α, β, γ, respectively, are denoted $R_{zyz}(\alpha, \beta, \gamma)$. Rotation estimation method using measured tip orientation is denoted $\hat{R}^\alpha$. Rotation estimation method using measured tip displacement is denoted $\hat{R}^{\Delta x}$. Base, tip and ground frames are denoted by B, T, G, respectively.

Robot Kinematics

Figure 2:
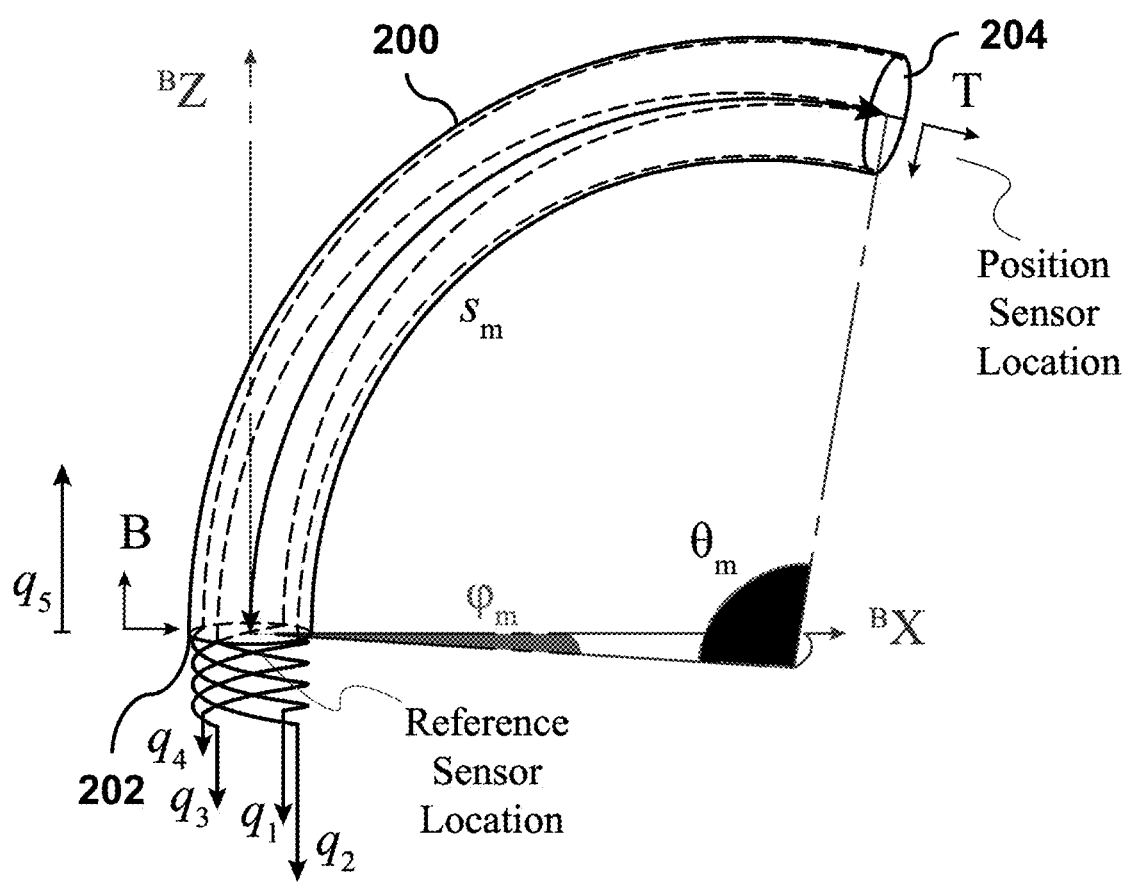
FIG. 2 is a schematic diagram of an articulating region of a four-tendon continuum manipulator.

The estimation methods used in embodiments of the present invention use a kinematic model of the 4-tendon continuum manipulator. FIG. 2 illustrates geometrical relationships of the constant curvature kinematics of a 4 tendon continuum manipulator, shown in its base frame, B. The kinematic model assumes constant curvature of the articulating region 200. The position and orientation of the distal tip relative to the robot's base is a function of its curvature. The base 202 is associated with base from B, while the tip 204 is associated with the tip frame T. The tendon displacements, $[q_1, \ldots, q_4]$ define the curvature of the articulated region. The curvature is parametrized by $[s_m, \theta_m, \phi_m]$, which is defined by the tendon displacements $[q_1, \ldots, q_4]$. The displacements, q, are measured relative to the motor position after tensioning the wires in the neutral, straight configuration. The insertion motor, $q_5$, translates the manipulator along the base's neutral Z axis, $^B Z$. The helical tendons through the catheter's passive region help decouple the passive and articulated regions. The four tendons are equally spaced 90° apart around the neutral axis at diameter of d=4.25 mm.

The tendon displacement is related to curvature as follows:

$$q_x = q_2 - q_4 \quad s_m = 35 \text{ mm} \tag{1}$$

$$q_y = q_3 - q_1 \quad \theta_m = \frac{1}{d}\sqrt{q_x^2 + q_y^2} \tag{2}$$

$$\phi_m = \arctan2(q_y, q_x) \tag{3}$$

The curvature is related to position and orientation, in base frame B, as follows:

$$x = \cos(\phi_m)\frac{s_m}{\theta_m}(1 - \cos(\theta_m)) \quad \alpha = \phi \tag{4}$$

$$y = \sin(\phi_m)\frac{s_m}{\theta_m}(1 - \cos(\theta_m)) \quad \beta = \theta \tag{5}$$

$$z = \frac{s_m}{\theta_m}(\theta_m) + q_5 \quad \gamma = -\phi \tag{6}$$

After the initial tensioning, this model assumes inextensible pull wires and an incompressible catheter body. It ignores internal friction and inertial effects. Without tension sensing, tension control was approximated by enforcing equal and opposite tendon displacement of antagonistic pairs, [($q_1$, $q_3$), ($q_2$, $q_4$)]. This tension control method is an oversimplification, and dead zones are apparent when the wire displacements change directions.

Model-Based Jacobian

In embodiments of the present invention, the methods to control the robot in task space (x, y, z) use the Jacobian. The Jacobian derivation is shown as follows:

The Jacobian is shown as the partial derivative of the catheter kinematics, as follows.

$$J = \frac{\partial x}{\partial [s, \theta, \phi]} \frac{\partial [s, \theta, \phi]}{\partial [q_x, q_y, q_5]} \frac{\partial [q_x, q_y, q_5]}{\partial q} \quad (7)$$

$$\frac{\partial [q_x, q_y, q_5]}{\partial q} = \begin{bmatrix} 1 & 0 & -1 & 0 & 0 \\ 0 & 1 & 0 & -1 & 0 \\ 0 & 0 & 0 & 0 & 1 \end{bmatrix} \quad (8)$$

$$\frac{\partial [s, \theta, \phi]}{\partial [q_x, q_y, q_5]} = \begin{bmatrix} 0 & 0 & 0 \\ \frac{q_x}{\theta d^2} & \frac{q_y}{\theta d^2} & 0 \\ -\frac{q_y}{q_x^2 + q_y^2} & \frac{q_x}{q_x^2 + q_y^2} & 0 \\ 0 & 0 & 1 \end{bmatrix} \quad (9)$$

$$\frac{\partial x}{\partial [s, \theta, \phi]}[:, 1] = \begin{bmatrix} \cos\phi(1-\cos\theta)/\theta \\ \sin\phi(1-\cos\theta)/\theta \\ \sin\theta/\theta \end{bmatrix} \quad (10)$$

$$\frac{\partial x}{\partial [s, \theta, \phi]}[:, 2] = \begin{bmatrix} \cos\phi s(\theta\sin\theta + \cos\theta - 1)/\theta^2 \\ \sin\phi s(\theta\sin\theta + \cos\theta - 1)/\theta^2 \\ s(\theta\cos\theta - \sin\theta)/\theta^2 \end{bmatrix} \quad (11)$$

$$\frac{\partial x}{\partial [s, \theta, \phi]}[:, 3] = \begin{bmatrix} -\sin\phi s(1-\cos\theta)/\theta \\ \cos\phi s(1-\cos\theta)/\theta \\ 1 \end{bmatrix} \quad (12)$$

where the [:,k] notation refers to the k-th column of the matrix.

Rotation Estimation

Figure 3:
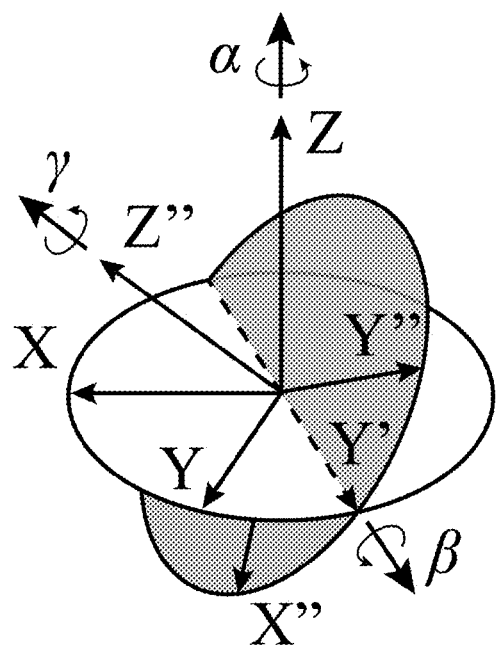
FIG. 3 is a diagram illustrating rotation about three Euler angles, α, β, γ, corresponding to the Z, Y', and Z" axes, respectively.

We now describe how the orientation of the base of the manipulator's articulating region is estimated. The rotation of the robot's base frame relative to the ground frame, $_B^G R$, is defined by the estimated Euler angles, [$\hat{\alpha}$, $\hat{\beta}$, $\hat{\gamma}$]. The $R_{zyz}(\alpha, \beta, \gamma)$ rotation matrix was chosen to describe the robot rotations; however, another choice of axes would lead to equivalent results. The $R_{zyz}(\alpha, \beta, \gamma)$ rotation describes an intrinsic rotation about the Z axis by $\alpha$, then about the resulting Y axis, shown as Y' axis, by $\beta$, and finally about the resulting Z axis, shown as Z", by $\gamma$, in FIG. 3. This rotation matrix transforms a vector in the X"Y"Z" reference frame into the XYZ frame. The $R_{zyz}(\alpha, \beta, \gamma)$ rotation matrix is given by $$R_{zyz}(\alpha, \beta, \gamma) = \begin{bmatrix} \cos\alpha\cos\beta\cos\gamma - \sin\alpha\sin\gamma & -\cos\alpha\cos\beta\sin\gamma - \sin\alpha\cos\gamma & \cos\alpha\sin\beta \\ \sin\alpha\cos\beta\cos\gamma + \cos\alpha\sin\gamma & -\sin\alpha\cos\beta\sin\gamma + \cos\alpha\cos\gamma & \sin\alpha\sin\beta \\ \sin\beta\cos\gamma & \sin\beta\sin\gamma & \cos\beta \end{bmatrix}$$

This $R_{zyz}(\alpha, \beta, \gamma)$ rotation matrix is used to rotate the model-based Jacobian in the following way:

$$^G\Delta x = _B^G R J_m(q) \Delta q \quad (13)$$

$$= R_{zyz}(\hat{\alpha}, \hat{\beta}, \hat{\gamma}) J_m(q) \Delta q \quad (14)$$

$$= \hat{J} \Delta q \quad (15)$$

Figure 4:
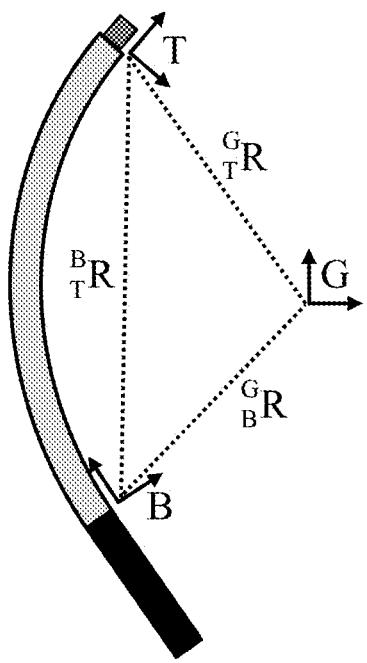
FIG. 4 is an illustration of an articulating region of a manipulator, showing relationship between ground frame, G, base frame, B, and tip frame, T, for one implementation of the estimation method.
Figure 5:
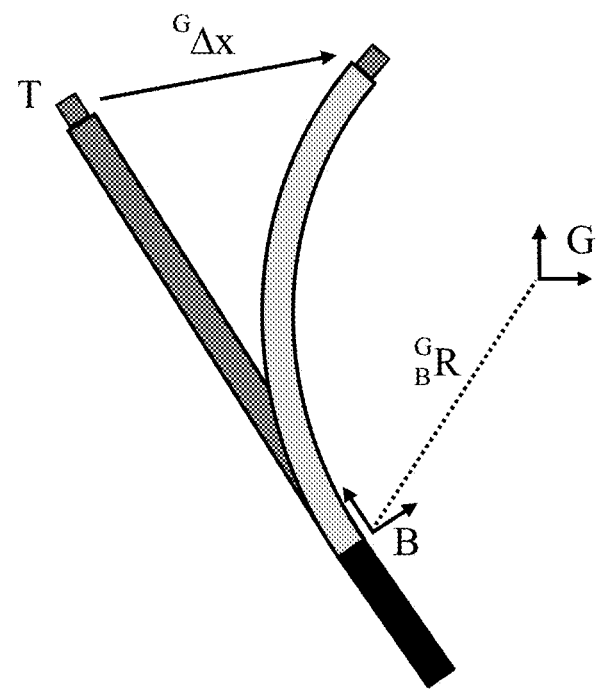
FIG. 5 is an illustration of an articulating region of a manipulator, showing the relationship of the measured tip displacement in the ground frame, which is used to estimate the rotation from ground to base in another implementation of the estimation method.

The implementation of the rotation estimation depends on the type of spatial attributes of the sensor that are measured. For example, FIG. 4 and FIG. 5 show two types of sensor spatial attributes corresponding to the two rotation estimation methods, $\hat{R}^\alpha$ and $\hat{R}^{\Delta x}$, respectively. In both cases, the estimated three Euler angles that define the state of the robot's rotation, $_B^G R$, are updated in real time. These two techniques will now be described in more detail.

Orientation Based Rotation Estimation ($\hat{R}^\alpha$)

In the $\hat{R}^\alpha$ implementation of FIG. 4, the base frame is calculated using the measured orientation of the robot's distal tip. FIG. 4 shows the relationship between ground frame, G, base frame, B, and tip frame, T. This orientation is transformed to the base through the curvature calculated from the model-based kinematics.

The magnetic position sensor measures the tip orientation in the global coordinate frame as azimuth, elevation, and roll. This orientation is converted into Euler angles, $_T^G[\alpha, \beta, \gamma]$, which define the rotation $_T^G R$ of the tip frame in the ground frame. The curvature of the catheter is converted into a rotation $_T^B R$ from the base to the tip. The base frame relative to the ground frame is then determined.

$$_T^G[\alpha, \beta, \gamma] = \begin{bmatrix} \text{azimuth} \\ \text{elevation} + \frac{\pi}{2} \\ \text{roll} \end{bmatrix}^T \quad (16)$$

$$_T^G R = R_{zyz}(_T^G[\alpha, \beta, \gamma]) \quad (17)$$

$$_T^B[\alpha, \beta, \gamma] = \begin{bmatrix} \arctan2(q_y, q_x) \\ \frac{1}{d}\sqrt{q_x^2 + q_y^2} \\ -\arctan2(q_y, q_x) \end{bmatrix}^T \quad (18)$$

$$_T^B R = R_{zyz}(_T^B[\alpha, \beta, \gamma]) \quad (19)$$

$$_B^G R = _T^G R (_T^B R)^T \quad (20)$$

$$[\hat{\alpha}, \hat{\beta}, \hat{\gamma}] = _B^G[\alpha, \beta, \gamma] \quad (21)$$

Displacement based Rotation Estimation ($\hat{R}^{\Delta x}$)

In the $\hat{R}^{\Delta x}$ implementation of FIG. 5, assuming the tip orientation is unknown, the base frame is determined using the measured change in position (displacement) of the distal tip. FIG. 5 shows the measured tip displacement in the ground frame, $^G\Delta x$, which is used to estimate the rotation from ground to base, $_B^G R$ The nonlinear relationship between change in position and the base's orientation is estimated using an unscented Kalman filter. Other embodiments can estimate the orientation using other Bayesian filters such as the extended Kalman filter, the particle filter, or the H-infinity filter.

Many clinical devices, including cardiac catheters, do not measure the orientation of the end effector. In this case, an estimate of the base rotation can be determined using the measured change in position, $[\Delta x, \Delta y, \Delta z]$. Due to the nonlinear relationship between the measured change in position and the base orientation, $[\hat{\alpha}, \hat{\beta}, \hat{\gamma}]$, we use non-linear estimation techniques, such as the extended and unscented Kalman filters. These filters develop a minimum mean squared error estimate of the state. The following formulation adheres to the convention for the measurement update step of the unscented Kalman filter (UKF):

$$x_{t+1} = x_t + v \quad (22)$$

$$y_t = h(x_t, q_t) + w \quad (23)$$

In this formulation, the state, x, is the three Euler angles describing the orientation of the robot base, $[\hat{\alpha}, \hat{\beta}, \hat{\gamma}]$. The motor displacements, q, are treated as known constants rather than part of the robot's state to be estimated.

$$x_t := [\hat{\alpha}_t, \hat{\beta}_t, \hat{\gamma}_t] \quad (24)$$

$$y_t := [\Delta x_t, \Delta y_t, \Delta z_t] \quad (25)$$

$$q_t := [\Delta q_{1t}, \ldots, \Delta q_{5t}, q_{1t}, \ldots, q_{5t}] \quad (26)$$

$$h(x_t, q_t) := R_{zyz}(\hat{\alpha}_t, \hat{\beta}_t, \hat{\gamma}_t) J_m(q_t) \Delta q_t \quad (27)$$

Because there is no a priori knowledge of how the base orientation will change over time, the time update step only serves to reintroduce uncertainty in the estimate of the Euler angles. The UKF parameters are set to: $\alpha=0.05$, $\beta=2$, $\kappa=0.1$, and the sensor noise, w, is empirically set to 0.25. To further mitigate noise, the measurement update is only performed after a displacement of of least 2.2 mm is measured, and the measured and expected displacements are normalized before each update.

The observability analysis of $\hat{R}^{\Delta x}$ shows that two linearly independent expected displacements enable the state to be fully observed. To determine the observability of the state, the linearized measurement matrix, H, is introduced. To clarify between the state, $x_t = [\alpha_t, \beta_t, \gamma_t]$, and the expected displacements along the coordinate axes, $\Delta x_m = [\Delta x, \Delta y, \Delta z]$, the state will be explicitly written as $[\alpha_t, \beta_t, \gamma_t]$ when possible.

$$H_1 = \frac{\partial h(x_1, q_1)}{\partial x_1} \quad (28)$$

$$= \frac{\partial R_{zyz}([\alpha_1, \beta_1, \gamma_1]) J_m(q_1) \Delta q_1}{\partial [\alpha_1, \beta_1, \gamma_1]} \quad (29)$$

$$= \frac{\partial R_{zyz}([\alpha_1, \beta_1, \gamma_1]) \Delta x_{m,1}}{\partial [\alpha_1, \beta_1, \gamma_1]} \quad (30)$$

$$\text{Rank}(H_1) = 2 \text{ if } \|\Delta x_{m,1}\| \neq 0 \quad (31)$$

Introducing another, linearly independent measurement at t=2, makes the observability matrix full rank. Note that the linearized time update, $F_t$, is the identity and is omitted.

$$O_2 = \begin{bmatrix} H_1 \\ H_2 \end{bmatrix} \quad (32)$$

$$\text{Rank}(O_2) = 3 \text{ if } \text{Rank}\left(\begin{bmatrix} \Delta x_{m,1}^\top \\ \Delta x_{m,2}^\top \end{bmatrix}\right) = 2 \quad (33)$$

In practice, this is accomplished with an insertion and a tendon displacement or two perpendicular tendon displacements.

Control Loop

Figure 6:
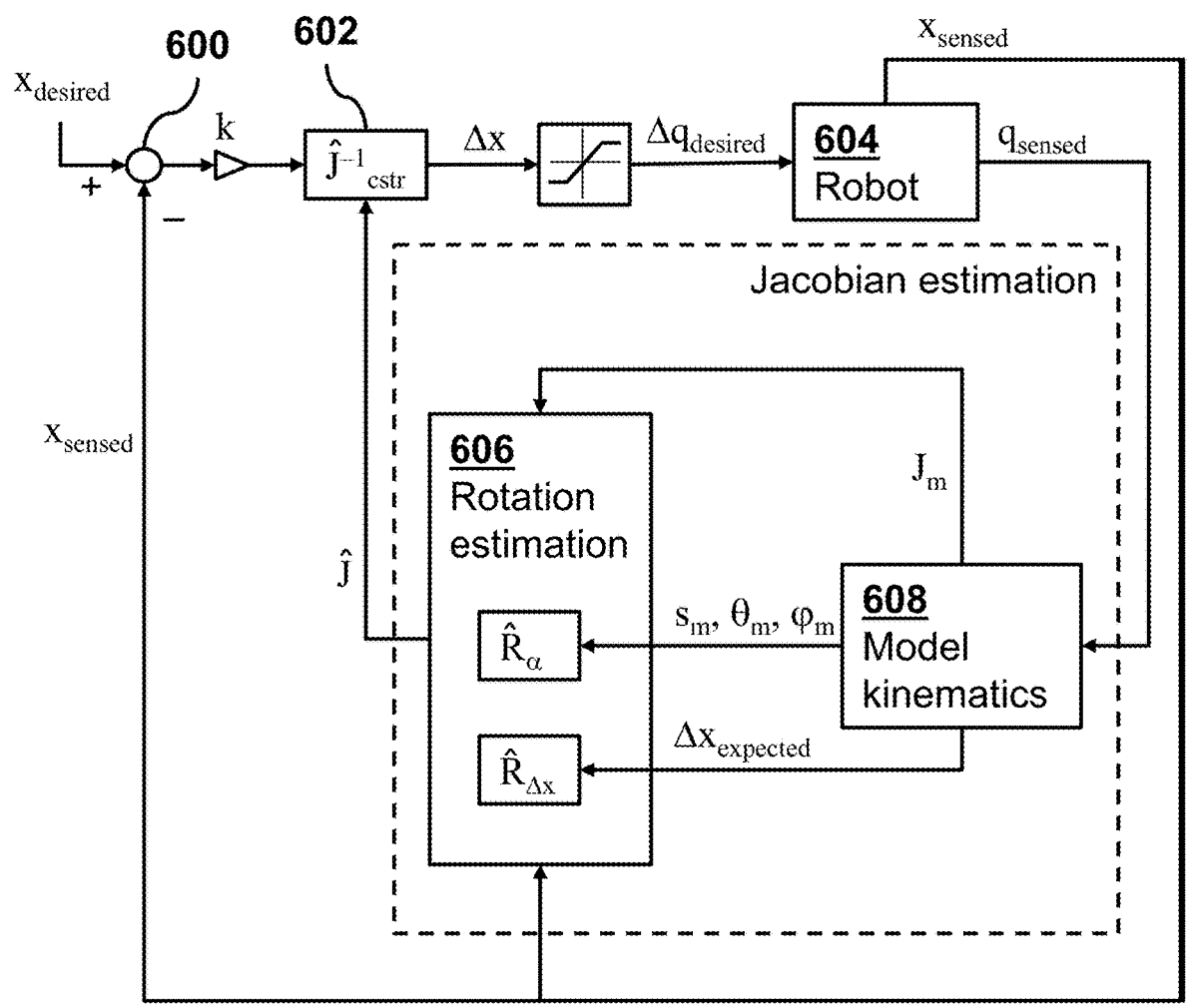
FIG. 6 is a schematic block diagram of a control loop used for manipulator control.

The control loop for autonomous navigation control of the manipulator in a task space is shown in FIG. 6.

The desired position in global coordinates $x_{desired}$ is compared at 600 to the current position measurement, $x_{sensed}$, using a proportional gain, k, of 1 to define the desired displacement, $\Delta x$. The current estimate of the base orientation and Jacobian, $\hat{J} = R_{zyz}(\hat{\alpha}, \hat{\beta}, \hat{\gamma}) J_m(q)$, is used at 602 to determine the desired motor velocity, $\Delta q_{desired}$, through an augmented Jacobian inverse, $J_{cstr}^{-1}$. The augmented Jacobian includes two rows to ensure the equal and opposite displacement of antagonistic tendons, $[(q_1, q_3), (q_2, q_4)]$.

$$\Delta q_{desired} = \begin{bmatrix} \hat{J} \\ 1 & 0 & 1 & 0 & 0 \\ 0 & 1 & 0 & 1 & 0 \end{bmatrix}^{-1} \begin{bmatrix} \Delta x \\ 0 \\ 0 \end{bmatrix} = J_{cstr}^{-1} \Delta x \quad (34)$$

The desired motor velocity $\Delta q_{desired}$ is automatically scaled down if this velocity exceeds the preset velocity threshold, and then it is used to control the robot 604.

In one implementation, robot 604 provides a sensed position $x_{sensed}$ from a sensor at the distal tip. Two sensed positions are used to determine a sensed displacement. This sensed position is fed back to the start of the loop at 600 and also provided to rotation estimation block 606. Sensed current motor position $q_{sensed}$ sensed from the robot 604 is sent to model kinematics block 608.

The model kinematics block 608 feeds the model-based Jacobian $J_m$ and the expected displacement $\Delta x_{expected}$ into the rotation estimation block 606, which then updates the estimate of the base orientation and the estimated Jacobian, $\hat{J}$.

In another implementation, robot 604 also provides a sensed orientation from a sensor at the distal tip. The method parallels the displacement method described above. This sensed orientation is provided to rotation estimation block 606 with the model-based Jacobian $J_m$ and the expected orientation $[s_m, \theta_m, \phi_m]$, which is calculated from the model kinematics block 608. The rotation estimation block 606 then updates the estimate of the base orientation and the estimated Jacobian, $\hat{J}$.

If the sensed position, $x_{sensed}$, is within $\epsilon$ of the desired point, the next way point in the trajectory is set as the desired position, $x_{desired}$. In this embodiment, the trajectory is assumed to be a list of positions for the robot to reach sequentially, which are determined prior to starting the control. In another embodiment, $x_{desired}$ is a function of $x_{sensed}$ and may change every cycle.

The control loop runs at 100 Hz, and all the parameters are filtered using a 5 Hz 2nd order low-pass Butterworth filter.

Experimental Testing

The inventors have tested the estimation techniques in an ideal setting in free space and in a silicone lung phantom. The estimation techniques are compared to both a static model-based technique (MBC) and a model-less control (MLC) method.

Figure 7:
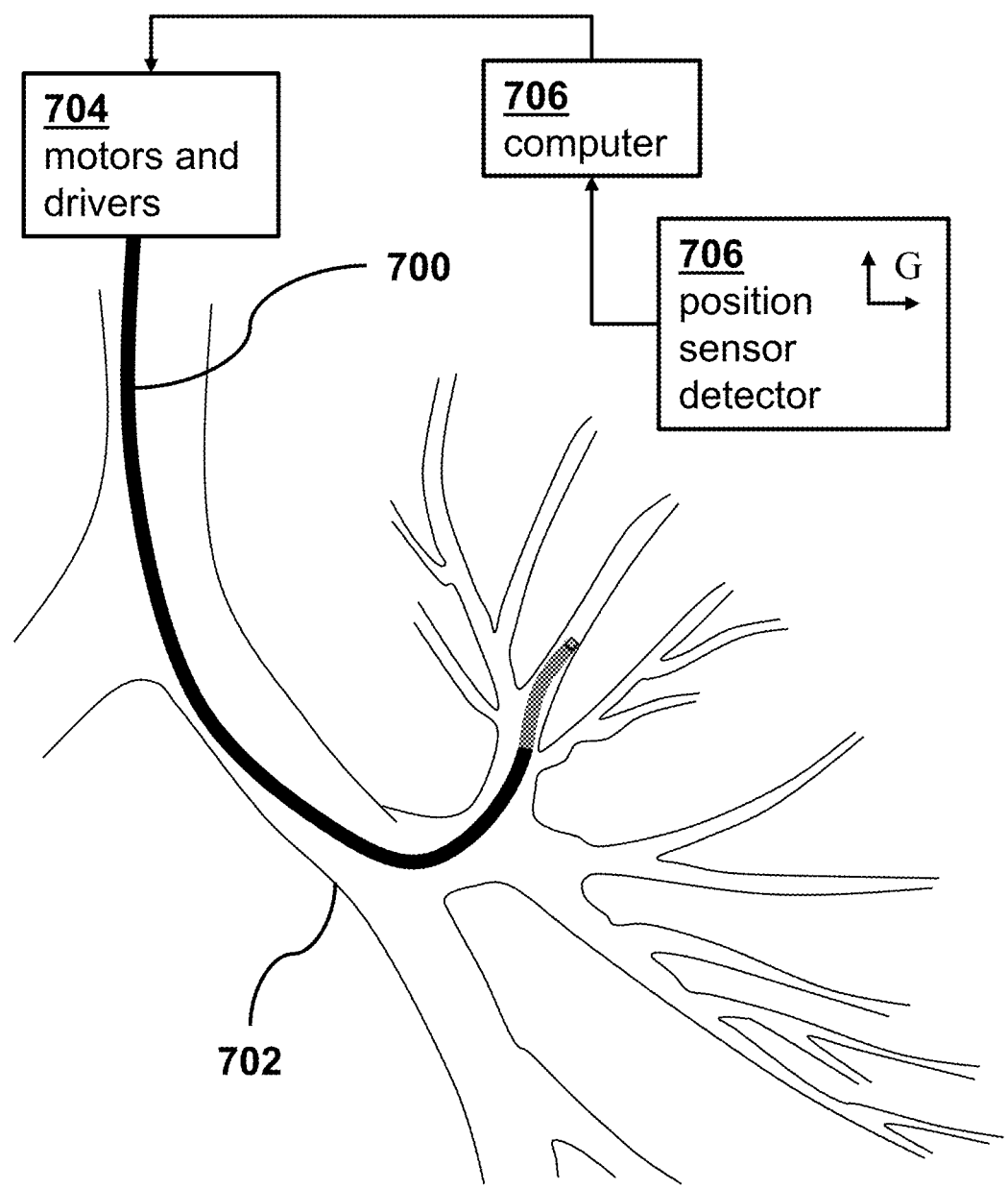
FIG. 7 is an illustration of an experimental setup for testing a lung navigation method.

FIG. 7 is a sketch of the experimental setup for the lung navigation task. The continuum manipulator 700 used for the test was a 16 French catheter with 4 articulating pull wires mounted on a linear slide. It was navigated through a silicone lung model 702. DC motors 704 drive each degree of freedom, controlled by digital servo drives. In the ground frame shown, $q_3$ and $q_1$ move the manipulator in ±Y, respectively. $q_4$ and $q_2$ move the manipulator in ±Z, respectively, and $q_5$ moves in +X.

A computer 706 with an i5 processor and 16 GB RAM ran the high-level control loop at 100 Hz. A distal electromagnetic position tracker 708 (trakSTAR, Ascension Technology/NDI, Ontario, Canada) provides real-time position sensing. For the test, a second sensor was fixed to the base of the articulating region to provide a reference orientation measurement. The RMS accuracy of the position sensors is 1.4 mm and 0.5 degrees.

Rotation in Free Space

Prior to navigating the constrained space of the lung, free space experiments were performed which showed the robot following a trajectory given a fixed, unknown base orientation. A square trajectory is defined in the global YZ plane, beginning with a 10 mm insertion along the X axis. The trajectory of way points are hit sequentially, moving to the next point after the tip enters within ±2 mm of the current way point.

Figure 8:
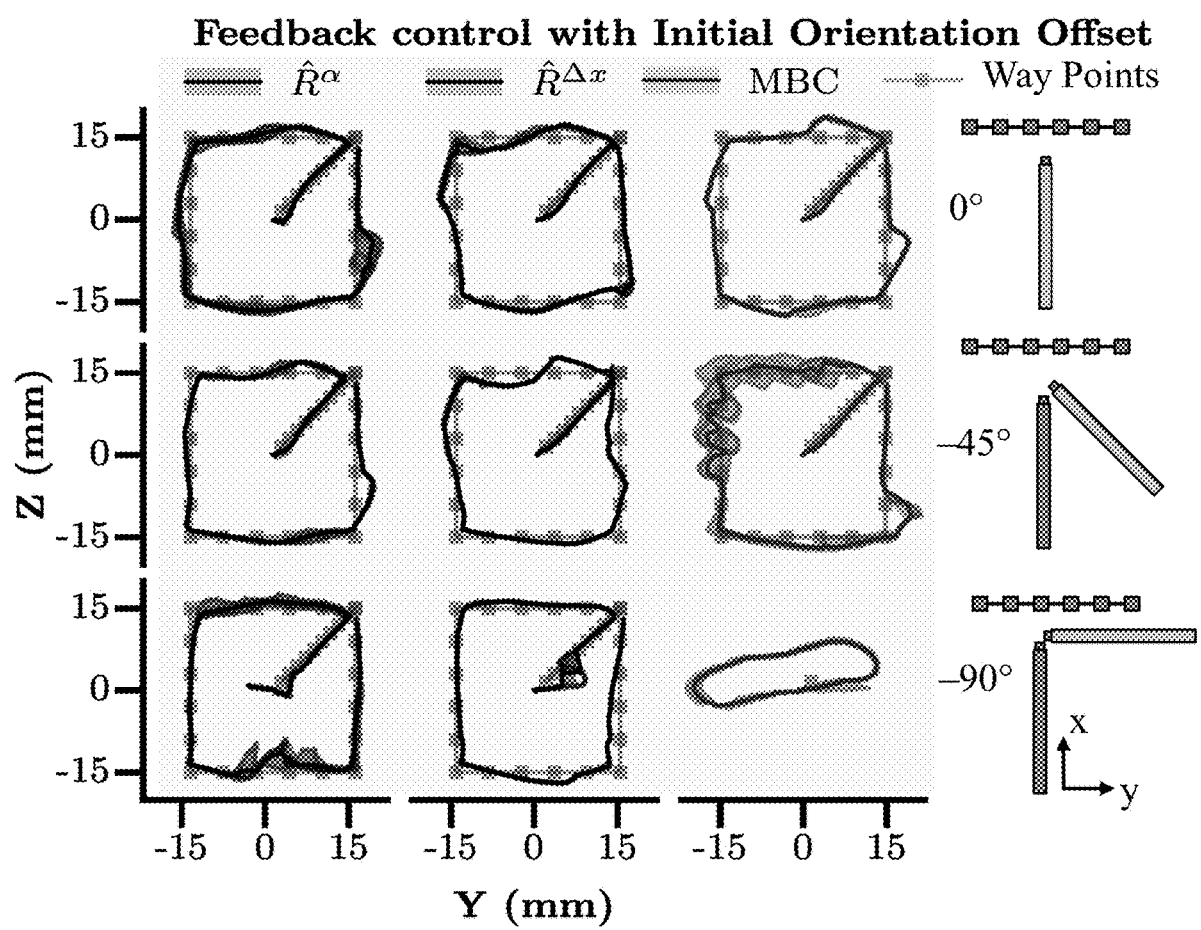
FIG. 8 is a plot showing a square trajectory in the global coordinate frame as prescribed with the robot configured in three orientations.

In FIG. 8, the two rotation estimation methods, $\hat{R}^\alpha$ and $\hat{R}^{\Delta x}$, are compared to the static kinematic model, MBC. The robot's tracking performance is shown with the robot configured in three orientation configurations with $\alpha=0°$, $-45°$, $-90°$, corresponding to the rotation of the robot model to the global coordinates about the global Z axis. For a given control method and orientation, four individual trials were performed.

The configurations show the effect of misalignments between the kinematic model's orientation and the true orientation. In each trial, the kinematic model's neutral axis aligns with the $\alpha=0°$ orientation, and the trace shows the average of 4 runs.

In each of the three configurations, the two rotation estimation methods, $\hat{R}^\alpha$ and $\hat{R}^{\Delta x}$, completed the trajectory by successfully estimating the base rotation. The static model fails to complete the trajectory when $\alpha=-90°$, and only the successfully reached way points are shown. In the case with $\alpha=-45°$, the static model completes the trajectory despite the improper mapping.

Figure 9:
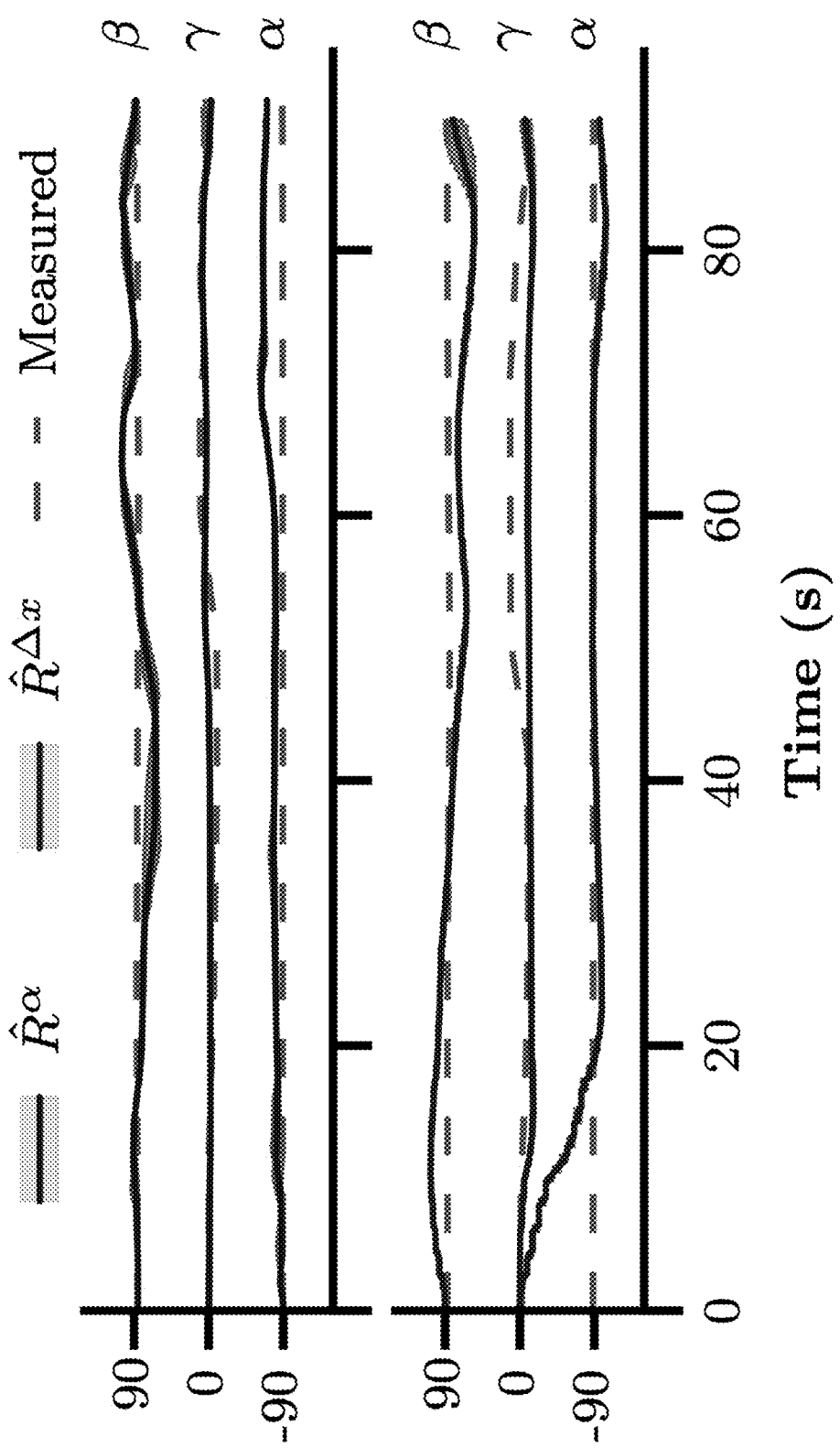
FIG. 9 is a graph of orientation estimates for one orientation configuration, where measured orientation is taken from the reference sensor fixed to the base of the robot.

FIG. 9 highlights the difference between $\hat{R}^\alpha$ and $\hat{R}^{\Delta x}$ orientation estimates in the $\alpha=-90°$ case. Each method's estimate of the base orientation is shown over the course of the trajectory when $\alpha=-90°$, as a representative trial. $\hat{R}^\alpha$ immediately estimates the appropriate orientation before any motion is made. Meanwhile, $\hat{R}^{\Delta x}$ converges to the appropriate estimate after about 20 seconds of attempting to reach the way points.

The measured orientation is taken from the reference sensor fixed to the base of the robot. The average and range of four runs are shown as a line and shaded region, respectively, in FIG. 8 and FIG. 9.

Lung Navigation

Figure 10:
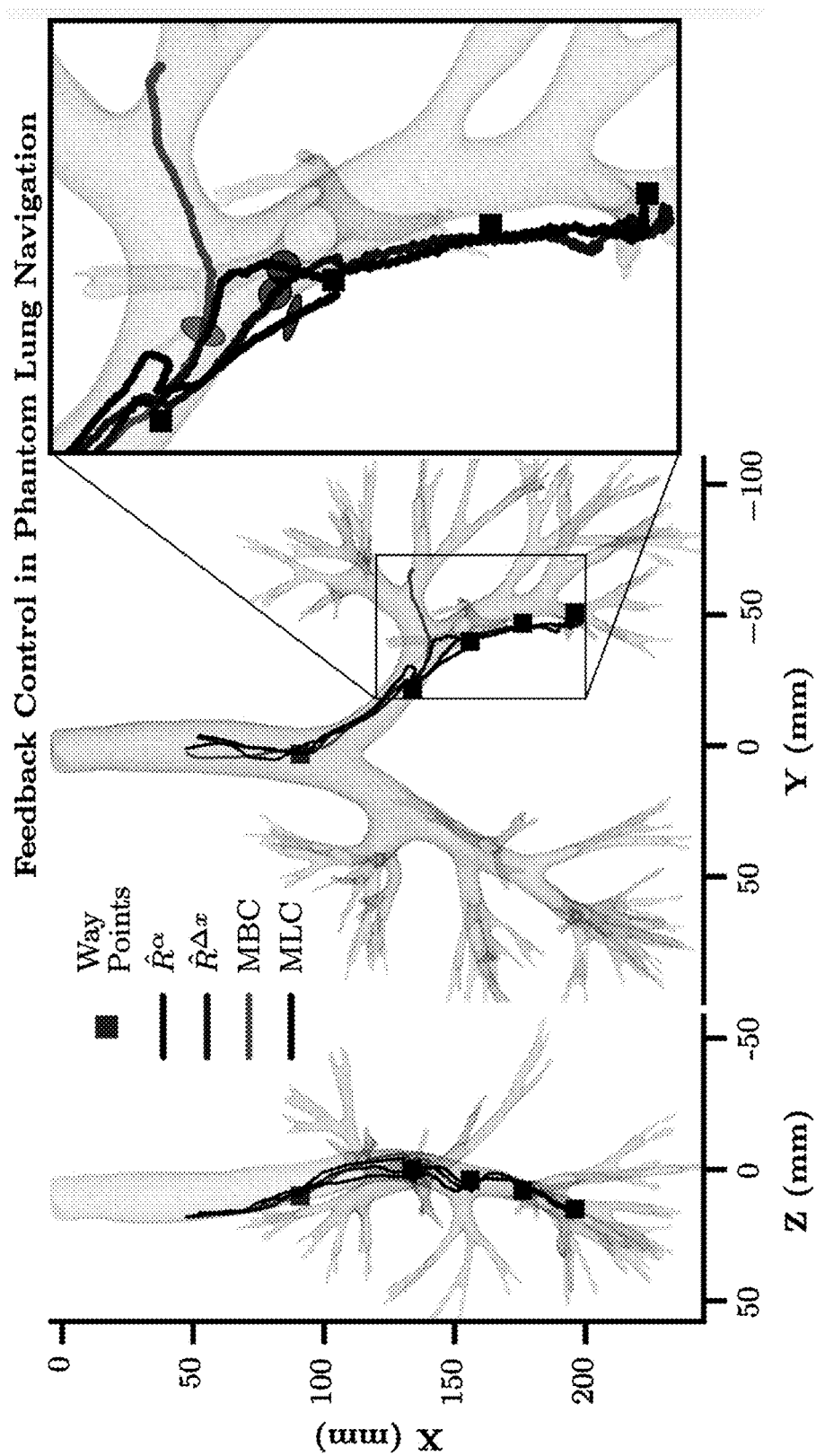
FIG. 10 is a plot showing the position traces of the distal tip of the robot during the lung navigation task for several control methods. The inset detail shows a 3× magnification of the left inferior lobe.

To simulate the constraints of a bronchoscopy procedure, the lung navigation task is performed in an anatomically accurate silicone phantom of the human airways (702, FIG. 7) (Bronchoscopy Training Model, Koken Co., Tokyo, Japan). The phantom is static and is registered to the position sensor's global reference frame. In the global frame, five way points are defined at anatomical junctions, reaching as far as the robot can reasonably fit. The rotation estimation methods $\hat{R}^\alpha$ and $\hat{R}^{\Delta x}$ are compared against MLC and MBC. A typical run for each method is shown in FIG. 10, which shows position traces of the distal tip of the robot in the lung navigation task. The detail shows a 3× magnification of the left inferior lobe.

The lung navigation task demonstrates the value of the rotation estimation schemes in highly constrained and tortuous environments. Both $\hat{R}^\alpha$ and $\hat{R}^{\Delta x}$ complete the full trajectory. In contrast, MLC reaches three way points before the robot steers into to the lung wall and pulls the tendon, $q_2$, to a dangerous level, resulting in the manual termination of the run. The MBC run is terminated after two way points, after driving into the wrong branch (see detail of FIG. 10).

Figure 11:
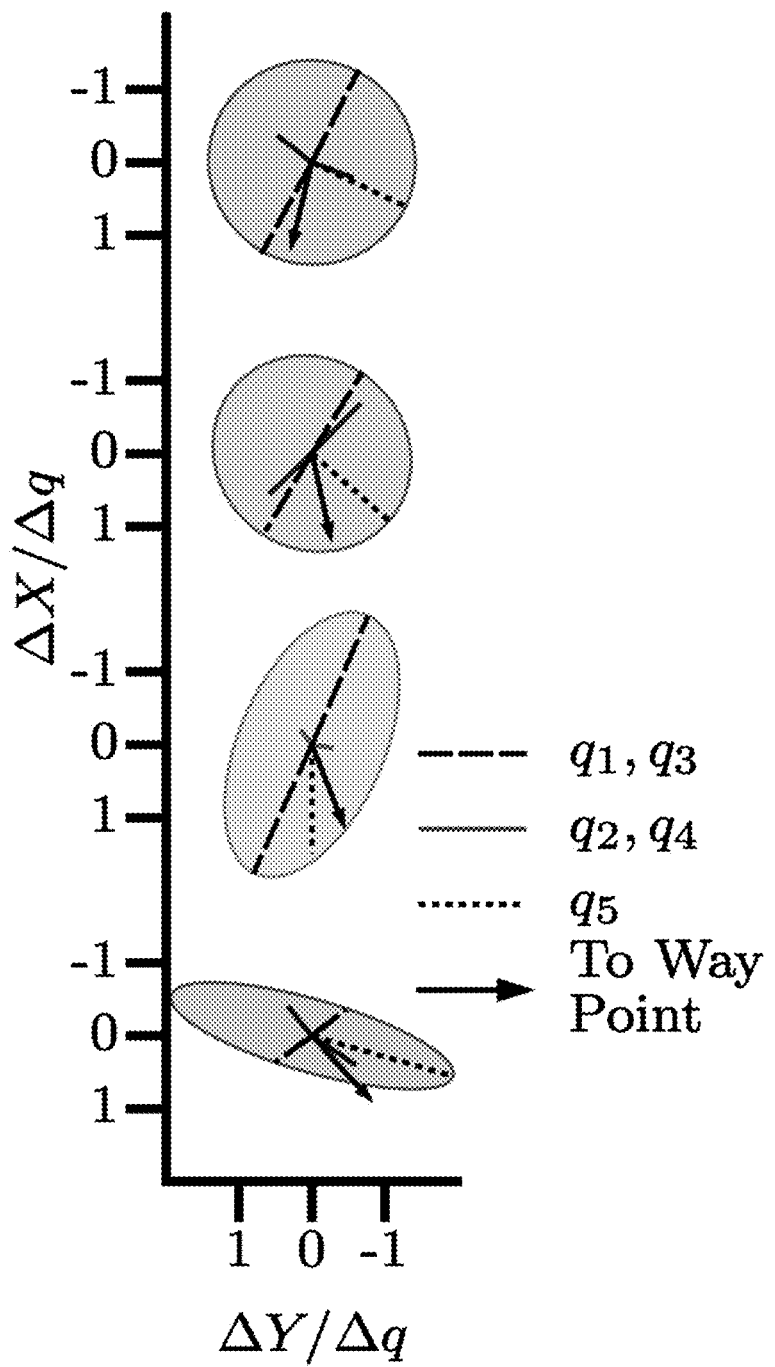
FIG. 11 is a graph showing the Jacobian ellipses at marked locations for several traces.

In FIG. 11, the Jacobian ellipses are shown for each model after they hit the second way point. Each ellipse shows the direction of the anticipated differential motion to the next way point given a motor displacement. There is a rotation about the roll axis differing between $\hat{R}^\alpha$ and $\hat{R}^{\Delta x}$. The model-less estimate is ill conditioned as the measured motion is masked by unsensed contact into the lung wall. The model-based Jacobian is unrotated, assuming the initial orientation.

Discussion

The navigation experiments in the lung phantom confirm that a rotation of the manipulator's base can approximate the unknown environmental constraints on a flexible continuum manipulator in the lung's airways. The experiments also show that $\hat{R}^\alpha$ and $\hat{R}^{\Delta x}$ are fairly similar in their outcomes, and superior to existing techniques. The key difference is that $\hat{R}^\alpha$ uses instantaneous orientation measurements, while $\hat{R}^{\Delta x}$ uses position displacements. Because of this difference, the two methods have different advantages. Using instantaneous orientation measurements makes $\hat{R}^\alpha$ robust to environmental disturbances such as a breathing, whereas $\hat{R}^{\Delta x}$ runs the risk of incorporating the environmental disturbance into the expected motion of the robot, resulting in inaccurate mappings. On the other hand, $\hat{R}^{\Delta x}$ can adapt better to a poor initial model of the manipulator, particularly when the mismatch involves a roll about the neutral axis.

In conclusion, the present invention provides a method of autonomous navigation of a continuum manipulator based on estimating the orientation of its articulating region base using a conventional distal sensor. As shown in the flowchart of FIG. 12, the method includes step 1200 which includes measuring spatial attributes of the sensor at the distal tip of the flexible tendon-driven continuum manipulator, wherein the spatial attributes include a position of the sensor at the distal tip; step 1202 which includes estimating an orientation of a base of the articulating region of the flexible tendon-driven continuum manipulator, wherein the orientation is estimated from a kinematic model of the flexible tendon-driven continuum manipulator and from the measured spatial attributes of the sensor at the distal tip of the flexible tendon-driven continuum manipulator; and step 1204 which includes controlling the flexible tendon-driven continuum manipulator in a task space using the estimated orientation of the base of the articulating region, a desired trajectory in the task space, and the position of the sensor at the distal tip. The method is applicable to flexible surgical robotics in minimally invasive surgeries.

The invention claimed is:

1. A method for autonomous closed loop control of a flexible tendon-driven continuum manipulator having a sensor at a distal tip and a passive region decoupled from an articulating region, the method comprising:

measuring spatial attributes of the sensor at the distal tip of the flexible tendon-driven continuum manipulator, wherein the spatial attributes include a position of the sensor at the distal tip;

estimating an orientation of a base of the articulating region of the flexible tendon-driven continuum manipulator, wherein the orientation is estimated from a kinematic model of the flexible tendon-driven continuum manipulator and from the measured spatial attributes of the sensor at the distal tip of the flexible tendon-driven continuum manipulator;

controlling the flexible tendon-driven continuum manipulator in a task space using the estimated orientation of the base of the articulating region, a desired trajectory in the task space, and the position of the sensor at the distal tip.

2. The method of claim 1 wherein the measured spatial attributes further include an orientation of the sensor at the distal tip of the flexible tendon-driven continuum manipulator; and wherein the orientation is estimated by transforming the orientation and the position to coordinates of the base through a curvature calculated from the kinematic model.

3. The method of claim 1 wherein the measured spatial attributes further include a displacement of the sensor at the distal tip of the flexible tendon-driven continuum manipulator; and wherein the orientation is estimated using a non-linear filter.

4. The method of claim 1 wherein the sensor at the distal tip is a magnetic sensor, impedance sensor, or optical sensor.

5. The method of claim 1 wherein the sensor at the distal tip is the only sensor on the flexible tendon-driven continuum manipulator.

* * * * *